US011198702B2

(12) United States Patent
Kuo et al.

(10) Patent No.: US 11,198,702 B2
(45) Date of Patent: Dec. 14, 2021

(54) METHOD FOR SEPARATING HYDROLYZED PRODUCT OF BIOMASS

(71) Applicant: Industrial Technology Research Institute, Hsinchu (TW)

(72) Inventors: Yen-Ting Kuo, Taipei (TW); Hou-Peng Wan, Taoyuan (TW); Tzu-Yueh Yang, Zhudong Township (TW); Chien-Yuan Su, Taipei (TW); Ming-Hua Wang, Taoyuan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 34 days.

(21) Appl. No.: 15/423,940

(22) Filed: Feb. 3, 2017

(65) Prior Publication Data

US 2017/0226144 A1 Aug. 10, 2017

Related U.S. Application Data

(60) Provisional application No. 62/291,164, filed on Feb. 4, 2016.

(30) Foreign Application Priority Data

Nov. 16, 2016 (TW) ................................ 105137396

(51) Int. Cl.
*C07H 3/02* (2006.01)

(52) U.S. Cl.
CPC ...................... *C07H 3/02* (2013.01)

(58) Field of Classification Search
CPC .... C07H 3/02; C07H 3/04; C07H 1/06; C02F 1/001
USPC ........................................................ 536/127
See application file for complete search history.

(56) References Cited

U.S. PATENT DOCUMENTS

| 4,411,787 A | 10/1983 | Riley |
| 4,452,640 A | 6/1984 | Chen et al. |
| 4,525,218 A | 6/1985 | Chen et al. |
| 4,637,835 A | 1/1987 | Nagle |
| 5,820,687 A | 10/1998 | Farone et al. |
| 5,968,362 A | 10/1999 | Russo, Jr. |
| 6,406,547 B1 | 6/2002 | Donovan et al. |
| 6,406,548 B1 | 6/2002 | Donovan et al. |
| 6,440,222 B1 | 8/2002 | Donovan et al. |
| 6,692,577 B2 | 2/2004 | Heikkilä et al. |
| 6,872,316 B2 | 3/2005 | Heikkilä et al. |
| 7,008,485 B2 | 3/2006 | Heikkila et al. |
| 7,009,076 B2 | 3/2006 | Paananen et al. |
| 7,037,378 B2 | 5/2006 | Jumppanen et al. |
| 7,374,684 B2 | 5/2008 | Gibson et al. |
| 7,611,872 B2 | 11/2009 | Beck et al. |
| 8,287,652 B2 | 10/2012 | Heikkilä et al. |
| 8,440,845 B2 | 5/2013 | Makkee et al. |
| 8,613,858 B2 | 12/2013 | Mänttäri et al. |
| 9,045,804 B2 | 6/2015 | Dumesic et al. |
| 2004/0006222 A1 | 1/2004 | Paananen et al. |
| 2004/0060868 A1 | 4/2004 | Heikkila et al. |
| 2005/0269265 A1 | 12/2005 | DeFrees |
| 2007/0113840 A1 | 5/2007 | Koivikko et al. |
| 2012/0220003 A1 | 8/2012 | Schwartz et al. |
| 2014/0090640 A1 | 4/2014 | Shih et al. |
| 2014/0151295 A1* | 6/2014 | Heon ................. C02F 1/28 210/609 |
| 2014/0261397 A1 | 9/2014 | Yang et al. |
| 2015/0167037 A1 | 6/2015 | Yamada et al. |
| 2015/0352501 A1 | 12/2015 | Ko et al. |
| 2015/0353977 A1 | 12/2015 | Yu et al. |

FOREIGN PATENT DOCUMENTS

| AU | 2014201107 A1 | 10/2014 | |
| CA | 2746504 A1 * | 6/2010 | ............. C08B 1/003 |
| CA | 2 846 855 A1 | 9/2014 | |
| CN | 1483086 A | 3/2004 | |
| CN | 1888080 A | 1/2007 | |
| CN | 101205561 A | 6/2008 | |
| CN | 101948452 A | 1/2011 | |
| CN | 102639722 A * | 8/2012 | ................ C12P 7/10 |
| CN | 103710472 A | 4/2014 | |
| CN | 104060000 A | 9/2014 | |
| CN | 104611476 A | 5/2015 | |
| EP | 2781605 A1 | 9/2014 | |
| GB | 1260826 | 1/1972 | |

(Continued)

OTHER PUBLICATIONS

Chinese Office Action and Search Report for Chinese Application No. 201710025708.6, dated Nov. 18, 2019.
Taiwanese Office Action and Search Report, dated Sep. 6, 2017, for Taiwanese Application No. 105137396.
Mohammad et al., "Nanofiltration of glucose solution containing salts: Effects of membrane characteristics, organic component and salts on retention", Journal of Food Engineering 97, 2010, p. 510-518.
Bargeman et al., "The effect of membrane characteristics on nanofiltration membrane performance during processing of practically saturated salt solutions", Journal of Membrane Science 485, 2015, p. 112-122.

(Continued)

*Primary Examiner* — Shaojia A Jiang
*Assistant Examiner* — Everett White
(74) *Attorney, Agent, or Firm* — Birch, Stewart, Kolasch & Birch, LLP

(57) ABSTRACT

A method for separating hydrolysis product of biomass is provided. The method includes providing a mixture solution containing a hydrolysis product of biomass and a divalent metal salt, adjusting the pH value of the mixture solution to between 1-4.6, and performing a filtering procedure on the mixture solution using a nanofiltration membrane to obtain a concentrated solution and a filtrate, wherein the concentrated solution mainly includes the hydrolysis product of biomass and the filtrate mainly includes the divalent metal salt.

10 Claims, No Drawings

(56) References Cited

FOREIGN PATENT DOCUMENTS

| JP | 4678831 B2 | 4/2011 |
|---|---|---|
| JP | 2011-202300 A | 10/2011 |
| RU | 2245714 C1 | 2/2005 |
| TW | 201412993 A | 4/2014 |
| TW | 201437222 A | 10/2014 |
| TW | 1476203 B | 3/2015 |
| WO | WO 02/053783 A1 | 7/2002 |
| WO | WO 2007/048879 A1 | 5/2007 |
| WO | WO 2013/110814 A1 | 8/2013 |

OTHER PUBLICATIONS

Bargeman et al., "The Effect of NaCl and glucose concentration on retentions for nanofiltration membranes processing concentrated solutions", Separation and Purification Technology 134, 2014, p. 46-57.

Almazán et al., "Nanofiltration of glucose: Analysis of parameters and membrane characterization", Chemical Engineering Research and Design 94, 2015, p. 485-493.

Wang et al., "The possibility of separating saccharides from a NaCl solution by using nanofiltratio in diafiltratio mode", Journal of Membrane Science 204, 2002, p. 271-281.

* cited by examiner

METHOD FOR SEPARATING HYDROLYZED PRODUCT OF BIOMASS

CROSS REFERENCE TO RELATED APPLICATIONS

This application claims the benefit of U.S. Provisional Application No. 62/291,164, filed on Feb. 4, 2016, and priority of Taiwan Patent Application No. 105137396, filed on Nov. 16, 2016, the entireties of which are incorporated by reference herein.

TECHNICAL FIELD

The technical field relates to a method for separating hydrolysis product of biomass including a filtering procedure performed with a nanofiltration membrane.

BACKGROUND

The world is facing problems such as the gradual extraction and depletion of petroleum reserves, and the earth's greenhouse effect continuing to expand. In order to ensure the sustainability of human life, it has become a world trend to gradually decrease the use of petrochemical energy and petroleum feedstock and to develop new sources of renewable energy and materials.

Lignocellulose is the main ingredient of biomass, which is the most abundant organic substance in the world. Lignocellulose mainly consists of 38-50% of cellulose, 23-32% of hemicelluloses, and 15-25% of lignin. Cellulose generates glucose through hydrolysis. Glucose can be converted to various biofuels or chemical raw materials such as alcohols (ethanol or butanol, etc.), organic acids (citric acid or lactic acid, etc.), polyalcohol monomers, sorbitol and 5-hydroxymethylfurfural (HMF) through biological or chemical methods. HMF is further converted into 2,5-dimethylfuran (DMF) through a hydrodeoxygenation process. DMF has advantages including a higher energy density than ethanol by 40%, a high boiling point, low toxicity, and poor miscibility with water. Many articles have explored the feasibility of using DMF to replace ethanol. In addition, DMF has the potential to replace fossil fuels or feedstocks, and is poised to become an important raw material in industry and energy in the future.

Regarding cellulose depolymerization technology, dilute acid hydrolysis is recently attracting a lot of attention in the field of chemical hydrolysis technology, generally with the use of sulfuric acid as a catalyst, and employing an operating temperature that is higher than 200° C. Therefore, the corrosion resistance requirements for the required equipment are high; simultaneously, the temperature of the dilute acid hydrolysis is high, resulting in formation of more fermentation inhibitors in the product and causing a low sugar yield. Concentrated acid hydrolysis can operate at lower temperatures and at normal pressure. However, there are problems with the strong corrosivity of the concentrated acid, complications in the post-purification processes of the hydrolysis sugar solution, and difficulties with recycling the acid solution, thereby increasing the restrictions on its industrial applications.

The prior art discloses the use of a zinc chloride solution with a high weight ratio to dissolve cellulose, followed by the addition of water, or the conversion of dilute acid-dissolved cellulose to glucose or HMF. However, the solution that is formed contains a large amount of zinc chloride. In addition, how to economically separate or recycle the hydrolysis product to separate it from the metal salts, and how to commercialize the entire process, are still problems that remain unsolved.

Therefore, the development of a novel method for separating hydrolysis product of biomass to solve the problems mentioned above is desirable.

SUMMARY

One embodiment of the disclosure provides a method for separating hydrolysis product of biomass. The method includes providing a mixture solution containing a hydrolysis product of biomass and a divalent metal salt, adjusting the pH value of the mixture solution to between 1-4.6, and performing a filtering procedure on the mixture solution using a nanofiltration membrane to obtain a concentrated solution and a filtrate, wherein the concentrated solution mainly includes the hydrolysis product of biomass and the filtrate mainly includes the divalent metal salt.

A detailed description is given in the following embodiments.

DETAILED DESCRIPTION

In the following detailed description, for the purposes of explanation, numerous specific details are set forth in order to provide a thorough understanding of the disclosed embodiments. It will be apparent, however, that one or more embodiments may be practiced without these specific details. In other instances, well-known structures and devices are shown schematically in order to simplify the drawing.

In order to solve the problems of poor separation between the hydrolysis product of biomass and the divalent metal salts, and poor recovery of the divalent metal salts caused by existing of high-weight-ratio salts and dilute acid-dissolved cellulose, the present disclosure adopts a filtering procedure using a nanofiltration membrane to purify the hydrolysis product of biomass and recover the metal salts.

In accordance with one embodiment of the disclosure, a method for separating hydrolysis product of biomass is provided. The method includes providing a mixture solution containing a hydrolysis product of biomass and a divalent metal salt, adjusting the pH value of the mixture solution to between 1-4.6, and performing a filtering procedure on the mixture solution using a nanofiltration membrane to obtain a concentrated solution and a filtrate. The concentrated solution includes the hydrolysis product of biomass and the filtrate includes the divalent metal salt.

In accordance with one embodiment of the disclosure, the hydrolysis product of biomass has a weight ratio of about 0.01-30 wt % in the mixture solution. The divalent metal salt has a weight ratio of about 0.1-20 wt % in the mixture solution.

In accordance with one embodiment of the disclosure, the pH value of the mixture solution is adjusted to between 1-4.6 to reduce the electrostatic interaction between the divalent metal salt, such as zinc chloride, and the membrane. While the pH value of the mixture solution is lower than 1, the durability of the membrane is thereby reduced, affecting the separation performance of the membrane under a high-pressure operation. While the pH value of the mixture solution is greater than 4.6, the separation effect between the hydrolysis product of biomass and the divalent metal salt cannot achieve the best condition. In addition, some of the divalent metal salt ions affect the separation efficiency due to precipitation characteristics.

In one embodiment of the disclosure, the hydrolysis product of biomass has a molecular weight of about 100-400 daltons. In one embodiment of the disclosure, the hydrolysis product of biomass comprises glucose, xylose, arabinose, cellobiose, 5-hydroxymethylfurfural (HMF), furfural (FF) or a combination thereof.

In one embodiment of the disclosure, the divalent metal salt comprises zinc chloride, calcium chloride, magnesium chloride or a combination thereof. After the filtering and recycling procedures, the divalent metal salts of zinc chloride, calcium chloride or magnesium chloride are reusable to save the cost of raw materials.

In one embodiment of the disclosure, the nanofiltration membrane has an intercept molecular weight of about 100-1,000 daltons or about 200-400 daltons (i.e. the nanofiltration membrane has about 100-1,000 amu (Daltons) molecular weight cut-off or about 200-400 amu (Daltons) molecular weight cut-off). While the molecular weight of the hydrolysis product of biomass is lower than 100 daltons, the nanofiltration membrane has poor separation effect on the hydrolysis product of biomass and the divalent metal salt. While the molecular weight of the hydrolysis product of biomass is greater than 1,000 daltons, such sizes exceed the scope capable of intercepting molecules of the nanofiltration membrane, resulting in poor separation effect. Then, use of an ultra-filtration procedure achieves the separation effect.

In one embodiment of the disclosure, the nanofiltration membrane comprises polyamide.

In one embodiment of the disclosure, the filtering procedure has an operating pressure of about 20-40 kg/cm$^2$. While the operating pressure is lower than 20 kg/cm$^2$, a high osmotic pressure formed from the metal salt concentration causes a few membrane fluxes; while the operating pressure is slightly larger than 20 kg/cm$^2$, the membrane flux is small, resulting in the need for more processing time, which cannot meet the requirement of regular industrial process; while the operating pressure is greater than 40 kg/cm$^2$, the structure of the membrane is destroyed and the separation effect of the membrane is affected due to the operating pressure exceeding the withstand pressure of the membrane itself.

In one embodiment of the disclosure, the present method for separating hydrolysis product of biomass further comprises performing at least one filtering procedure on the concentrated solution. The hydrolysis product of biomass, such as glucose or xylose, has a weight ratio of about 1-10 wt % in the concentrated solution.

In one embodiment of the disclosure, the present method for separating hydrolysis product of biomass further comprises performing at least one filtering procedure on the filtrate. The divalent metal salt has a weight ratio of about 0.1-20 wt % (which is referred to the concentration obtained after the pH adjustment, the operating pressure adjustment and the filtering procedure) in the filtrate. While the concentration of the metal salt in the concentrated solution is reduced to a certain concentration, the concentrated solution is used in the back-end sugar fermentation process.

EXAMPLE 1

Preparation of the Hydrolysis Product of Biomass (1)

Hydrochloric acid and zinc chloride (ZnCl$_2$) were mixed and stirred at room temperature under a normal pressure to form a mixing solution (containing 2 wt % of hydrochloric acid and 257 g of ZnCl$_2$). 14.21 g of bagasse was added to 100 g of the mixing solution to proceed to a dissolution reaction (temperature: 98° C.; time: 10 minutes). After the bagasse was completely dissolved, a reddish brown homogeneous liquid was obtained. Next, 100 g of hydrochloric acid aqueous solution (2 wt %) was added to the reddish brown homogeneous liquid (temperature: 100° C.; time: 10 minutes). The pH value of the mixing solution was adjusted to 1-2. After a solid-liquid separation procedure, a concentrated solution (containing hydrolysis product of biomass) and a filtrate (containing divalent metal salts) were obtained. Next, the total weight of the reducing sugar was determined by high performance liquid chromatography (HPLC), and the yield of the reducing sugar was calculated. The reducing sugars may include glucose, xylose, mannose, arabinose and oligosaccharides thereof. 7.72 g of the reducing sugar was obtained in the yield of 86.5 wt %, as shown in Table 1.

EXAMPLE 2

Preparation of the Hydrolysis Product of Biomass (2)

Hydrochloric acid and zinc chloride (ZnCl$_2$) were mixed and stirred at room temperature under a normal pressure to form a mixing solution (containing 2 wt % of hydrochloric acid and 257 g of ZnCl$_2$). 40 g of bagasse was added to 100 g of the mixing solution to proceed to a dissolution reaction (temperature: 98° C.; time: 10 minutes). After the bagasse was completely dissolved, a reddish brown homogeneous liquid was obtained. Next, 100 g of hydrochloric acid aqueous solution (2 wt %) was added to the reddish brown homogeneous liquid (temperature: 100° C.; time: 10 minutes). The pH value of the mixing solution was adjusted to 1-2. After a solid-liquid separation procedure, a concentrated solution (containing hydrolysis product of biomass) and a filtrate (containing divalent metal salts) were obtained. Next, the total weight of the reducing sugar was determined by high performance liquid chromatography (HPLC), and the yield of the reducing sugar was calculated. The reducing sugars may include glucose, xylose, mannose, arabinose and oligosaccharides thereof. 18.81 g of the reducing sugar was obtained in the yield of 78.8 wt %, as shown in Table 1.

EXAMPLE 3

Preparation of the Hydrolysis Product of Biomass (3)

Hydrochloric acid and zinc chloride (ZnCl$_2$) were mixed and stirred at room temperature under a normal pressure to form a mixing solution (containing 2 wt % of hydrochloric acid and 257 g of ZnCl$_2$). 50 g of bagasse was added to 100 g of the mixing solution to proceed to a dissolution reaction (temperature: 98° C.; time: 10 minutes). After the bagasse was completely dissolved, a reddish brown homogeneous liquid was obtained. Next, 100 g of hydrochloric acid aqueous solution (2 wt %) was added to the reddish brown homogeneous liquid (temperature: 100° C.; time: 10 minutes). The pH value of the mixing solution was adjusted to 1-2. After a solid-liquid separation procedure, a concentrated solution (containing hydrolysis product of biomass) and a filtrate (containing divalent metal salts) were obtained. Next, the total weight of the reducing sugar was determined by high performance liquid chromatography (HPLC), and the yield of the reducing sugar was calculated. The reducing sugars may include glucose, xylose, mannose, arabinose and oligosaccharides thereof. 21.02 g of the reducing sugar was obtained in the yield of 66.9 wt %, as shown in Table 1.

EXAMPLE 4

Preparation of the Hydrolysis Product of Biomass (4)

Hydrochloric acid and calcium chloride (CaCl$_2$) were mixed and stirred at room temperature under a normal pressure to form a mixing solution (containing 2 wt % of hydrochloric acid and 257 g of CaCl$_2$). 14.21 g of bagasse was added to 100 g of the mixing solution to proceed to a dissolution reaction (temperature: 98° C.; time: 10 minutes). After the bagasse was completely dissolved, a reddish brown homogeneous liquid was obtained. Next, 100 g of hydrochloric acid aqueous solution (2 wt %) was added to the reddish brown homogeneous liquid (temperature: 100° C.; time: 10 minutes). The pH value of the mixing solution was adjusted to 1-2. After a solid-liquid separation procedure, a concentrated solution (containing hydrolysis product of biomass) and a filtrate (containing divalent metal salts) were obtained. Next, the total weight of the reducing sugar was determined by high performance liquid chromatography (HPLC), and the yield of the reducing sugar was calculated.

EXAMPLE 5

Preparation of the Hydrolysis Product of Biomass (5)

Hydrochloric acid and magnesium chloride (MgCl$_2$) were mixed and stirred at room temperature under a normal pressure to form a mixing solution (containing 2 wt % of hydrochloric acid and 257 g of MgCl$_2$). 14.21 g of bagasse was added to 100 g of the mixing solution to proceed to a dissolution reaction (temperature: 98° C.; time: 10 minutes). After the bagasse was completely dissolved, a reddish brown homogeneous liquid was obtained. Next, 100 g of hydrochloric acid aqueous solution (2 wt %) was added to the reddish brown homogeneous liquid (temperature: 100° C.; time: 10 minutes). The pH value of the mixing solution was adjusted to 1-2. After a solid-liquid separation procedure, a concentrated solution (containing hydrolysis product of biomass) and a filtrate (containing divalent metal salts) were obtained. Next, the total weight of the reducing sugar was determined by high performance liquid chromatography (HPLC), and the yield of the reducing sugar was calculated.

TABLE 1

| Examples | Bagasse (g) | Dissolution temp. (° C.) | Dissolution time (min) | Hydrolysis temp. (° C.) | Hydrolysis time (min) | Yield of reducing sugar (%) |
| --- | --- | --- | --- | --- | --- | --- |
| 1 | 14.21 | 98 | 10 | 100 | 10 | 86.5 |
| 2 | 40 | 98 | 10 | 100 | 10 | 78.8 |
| 3 | 50 | 98 | 10 | 100 | 10 | 66.9 |

EXAMPLE 6

Effect of Divalent Metal Salts on Separation Efficiency (1)

A filtering procedure (total feed: 30 kg; operating pressure: 35 kg/cm$^2$; pH: 2) was performed on the hydrolysis sugar solution (glucose-mixed simulation solution concentration: 3 wt %; zinc chloride concentration: 12 wt %) with a nanofiltration membrane (DOW FILMTEC™; model: NF-40). The ratio of the concentrated solution and the filtrate was controlled to 4. After the filtering procedure, the separation efficiency of the zinc chloride (ZnCl$_2$) was 7.9, as shown in Table 2.

EXAMPLE 7

Effect of Divalent Metal Salts on Separation Efficiency (2)

A filtering procedure (total feed: 30 kg; operating pressure: 35 kg/cm$^2$; pH: 2) was performed on the hydrolysis sugar solution (glucose-mixed simulation solution concentration: 3 wt %; calcium chloride concentration: 12 wt %) with a nanofiltration membrane (DOW FILMTEC™; model: NF-40). The ratio of the concentrated solution and the filtrate was controlled to 4. After the filtering procedure, the separation efficiency of the calcium chloride (CaCl$_2$) was 1.7, as shown in Table 2.

EXAMPLE 8

Effect of Divalent Metal Salts on Separation Efficiency (3)

A filtering procedure (total feed: 30 kg; operating pressure: 35 kg/cm$^2$; pH: 2) was performed on the hydrolysis sugar solution (glucose-mixed simulation solution concentration: 3 wt %; magnesium chloride concentration: 12 wt %) with a nanofiltration membrane (DOW FILMTEC™; model: NF-40). The ratio of the concentrated solution and the filtrate was controlled to 4. After the filtering procedure, the separation efficiency of the magnesium chloride (MgCl$_2$) was 2.2, as shown in Table 2.

TABLE 2

| Divalent metal salts | Example 6 | Example 7 | Example 8 |
| --- | --- | --- | --- |
| pH value | 2 | 2 | 2 |
| Separation efficiency | 7.9 | 1.7 | 2.2 |

The separation efficiency was defined as follows:

Separation efficiency=Concentration ratio of glucose in concentrated solution and filtrate/Concentration ratio of zinc chloride in concentrated solution and filtrate Table 2 shows that the separation efficiency of each of the divalent metal salts was greater than 1. The definition of the separation efficiency is that the concentration ratio of glucose in a concentrated solution and a filtrate is divided by the concentration ratio of divalent metal salts in the concentrated solution and the filtrate. While the separation efficiency was greater than 1, it is represented that, using the method for separating hydrolysis product of biomass in the Examples of the present disclosure, for the hydrolysis sugar solution, sugar substance with higher concentration (i.e. purity improvement) was obtained in the concentrated solution, and a metal salt solution with higher purity was obtained in the filtrate. That is, an optimal separation effect between the metal salts and the sugar was achieved.

EXAMPLE 9

Effect of pH Adjustment on Separation Efficiency of Divalent Metal Salts (1)

A filtering procedure (total feed: 30 kg; operating pressure: 35 kg/cm$^2$; pH: 1) was performed on the hydrolysis sugar solution (glucose concentration: 3 wt %; zinc chloride concentration: 12 wt %) with a nanofiltration membrane (DOW FILMTEC™; model: NF-40). The ratio of the concentrated solution and the filtrate was controlled to 4. After the filtering procedure, the separation efficiency of the zinc chloride ($ZnCl_2$) was 9.7, as shown in Table 3.

EXAMPLE 10

Effect of pH Adjustment on Separation Efficiency of Divalent Metal Salts (2)

A filtering procedure (total feed: 30 kg; operating pressure: 35 kg/cm$^2$; pH: 2) was performed on the hydrolysis sugar solution (glucose concentration: 3 wt %; zinc chloride concentration: 12 wt %) with a nanofiltration membrane (DOW FILMTEC™; model: NF-40). The ratio of the concentrated solution and the filtrate was controlled to 4. After the filtering procedure, the separation efficiency of the zinc chloride ($ZnCl_2$) was 7.9, as shown in Table 3.

EXAMPLE 11

Effect of pH Adjustment on Separation Efficiency of Divalent Metal Salts (3)

A filtering procedure (total feed: 30 kg; operating pressure: 35 kg/cm$^2$; pH: 4) was performed on the hydrolysis sugar solution (glucose concentration: 3 wt %; zinc chloride concentration: 12 wt %) with a nanofiltration membrane (DOW FILMTEC™; model: NF-40). The ratio of the concentrated solution and the filtrate was controlled to 4. After the filtering procedure, the separation efficiency of the zinc chloride ($ZnCl_2$) was 5.8, as shown in Table 3.

EXAMPLE 12

Effect of pH Adjustment on Separation Efficiency of Divalent Metal Salts (4)

A filtering procedure (total feed: 30 kg; operating pressure: 35 kg/cm$^2$; pH: 4.6) was performed on the hydrolysis sugar solution (glucose concentration: 3 wt %; zinc chloride concentration: 12 wt %) with a nanofiltration membrane (DOW FILMTEC™; model: NF-40). The ratio of the concentrated solution and the filtrate was controlled to 4. After the filtering procedure, the separation efficiency of the zinc chloride ($ZnCl_2$) was 2.5, as shown in Table 3.

Comparative Example 1

A filtering procedure (total feed: 30 kg; operating pressure: 35 kg/cm$^2$; pH: >4.6) was performed on the hydrolysis sugar solution (glucose concentration: 3 wt %; zinc chloride concentration: 12 wt %) with a nanofiltration membrane (DOW FILMTEC™; model: NF-40). Since zinc chloride is a weakly acidic salt, while it was dissolved in water, hydrogen ions were released, causing the pH of zinc chloride dissolved in water to be around 4.6. In order to adjust the pH to become a neutral solution (pH=7) or even an alkaline solution (pH>7), it is necessary to add other alkaline solutions such as sodium hydroxide, etc. However, this increased the cost burden of the future amplification processes. Since the chemical nature of the zinc hydroxide salt itself was that zinc hydroxide precipitation is easily generated at pH>7, it may also cause rear-end separation problems.

TABLE 3

| Examples | pH value | Separation efficiency |
|---|---|---|
| 9 | 1 | 9.7 |
| 10 | 2 | 7.9 |
| 11 | 4 | 5.8 |
| 12 | 4.6 | 2.5 |
| Comparative Example 1 | >4.6 | — |

Table 3 shows that the pH adjustment improved the separation efficiency of zinc chloride in the membrane. While the hydrolysis sugar solution was in a specific pH condition, the separation efficiency of the zinc chloride in the membrane was increased to more than 2 times by altering the electrostatic repulsion between zinc chloride hydrate and the membrane to increase the membrane flux of the zinc chloride (reducing the blocking effect). Further, it is further understood from Table 3 that the separation efficiency also increased with decreasing pH values.

EXAMPLE 13

The Filtering Procedure of the Membrane (1)

A filtering procedure (total feed: 30 kg; operating pressure: 30 kg/cm$^2$; pH: 4.6) was performed on a hydrolysis sugar solution (total sugar concentration: 4.3 wt %; zinc chloride concentration: 6.6 wt %) with a nanofiltration membrane (DOW FILMTEC™; model: NF-270) to obtain 6 kg of a concentrated solution and 24 kg of a filtrate. The ratio of the concentrated solution and the filtrate was controlled to 4. After the filtering procedure, the separation efficiency of the glucose and the zinc chloride ($ZnCl_2$) was 1.85. It is shown that the filtrating procedure of the membrane contributed to the concentration of sugar and the effect of separating zinc chloride.

EXAMPLE 14

The Filtering Procedure of the Membrane (2)

A filtering procedure (total feed: 24 kg; operating pressure: 30 kg/cm$^2$; pH: 4.6) was performed on a hydrolysis sugar solution (total sugar concentration: 1.3 wt %; zinc chloride concentration: 6.0 wt %) with a nanofiltration membrane (DOW FILMTEC™; model: NF-270) to obtain 6 kg of a concentrated solution and 18 kg of a filtrate. The ratio of the concentrated solution and the filtrate was controlled to 4. After the filtering procedure, the separation efficiency of the glucose and the zinc chloride ($ZnCl_2$) was 2.46. It is shown that the filtrating procedure of the membrane contributed to the concentration of sugar and the effect of separating zinc chloride.

EXAMPLE 15

The Filtering Procedure of the Membrane (3)

A filtering procedure (total feed: 25 kg; operating pressure: 35 kg/cm$^2$; pH: 1) was performed on a hydrolysis sugar solution (total sugar concentration: 6.4 wt %; zinc chloride concentration: 16.3 wt %) with a nanofiltration membrane (DOW FILMTEC™; model: NF-270) to obtain 10 kg of a concentrated solution. Next, 15 kg of pure water was added to the concentrated solution. Another filtering procedure (including adding water and filtrating by membrane) using a nanofiltration membrane was repeated three times to obtain 10 kg of a concentrated solution (total sugar concentration: 7.2 wt %; zinc chloride concentration: 4.1 wt %) and 44 kg of a filtrate (total sugar concentration: 1.3 wt %; zinc chloride concentration: 8.1 wt %). After the filtering procedures, in the concentrated solution, the total sugar concentration was increased from 6.4 wt % to 7.2 wt %, the zinc chloride concentration was decreased from 16.3 wt % to 4.1 wt %, and the purity of sugar was increased from 28.2% to 63.7%. It is shown that the filtrating procedures of the membrane contributed to the concentration of sugar and the effect of separating zinc chloride.

EXAMPLE 16

The Filtering Procedure of the Membrane (4)

A filtering procedure (total feed: 44 kg; operating pressure: 35 kg/cm$^2$; pH: 2) was performed on a hydrolysis sugar solution (total sugar concentration: 1.3 wt %; zinc chloride concentration: 8.1 wt %) with a nanofiltration membrane (DOW FILMTEC™; model: NF-270) to obtain 9 kg of a concentrated solution and 35 kg of a filtrate. The ratio of the concentrated solution and the filtrate was controlled to 4. After the filtering procedure, the separation efficiency of the glucose and the zinc chloride (ZnCl$_2$) was 4.85. It is shown that the filtrating procedure of the membrane contributed to the concentration of sugar and the effect of separating zinc chloride.

EXAMPLE 17

Effect of Operating Pressure Adjustment on Separation Efficiency of Divalent Metal Salts (1)

A filtering procedure (total feed: 26 kg; operating pressure: 26 kg/cm$^2$; pH: 4.6) was performed on the hydrolysis sugar solution (glucose concentration: 3 wt %; zinc chloride concentration: 12 wt %) with a nanofiltration membrane (DOW FILMTEC™; model: NF-40). The ratio of the concentrated solution and the filtrate was controlled to 4. After the filtering procedure, the separation efficiency of the glucose and the zinc chloride (ZnCl$_2$) was 1.77, as shown in Table 4.

EXAMPLE 18

Effect of Operating Pressure Adjustment on Separation Efficiency of Divalent Metal Salts (2)

A filtering procedure (total feed: 30 kg; operating pressure: 30 kg/cm$^2$; pH: 4.6) was performed on the hydrolysis sugar solution (glucose concentration: 3 wt %; zinc chloride concentration: 12 wt %) with a nanofiltration membrane (DOW FILMTEC™; model: NF-40). The ratio of the concentrated solution and the filtrate was controlled to 4. After the filtering procedure, the separation efficiency of the glucose and the zinc chloride (ZnCl$_2$) was 2.40, as shown in Table 4.

EXAMPLE 19

Effect of Operating Pressure Adjustment on Separation Efficiency of Divalent Metal Salts (3)

A filtering procedure (total feed: 30 kg; operating pressure: 35 kg/cm$^2$; pH: 4.6) was performed on the hydrolysis sugar solution (glucose concentration: 3 wt %; zinc chloride concentration: 12 wt %) with a nanofiltration membrane (DOW FILMTEC™; model: NF-40). The ratio of the concentrated solution and the filtrate was controlled to 4. After the filtering procedure, the separation efficiency of the glucose and the zinc chloride (ZnCl$_2$) was 2.55, as shown in Table 4.

EXAMPLE 20

Effect of Operating Pressure Adjustment on Separation Efficiency of Divalent Metal Salts (4)

A filtering procedure (total feed: 30 kg; operating pressure: 40 kg/cm$^2$; pH: 4.6) was performed on the hydrolysis sugar solution (glucose concentration: 3 wt %; zinc chloride concentration: 12 wt %) with a nanofiltration membrane (DOW FILMTEC™; model: NF-40). The ratio of the concentrated solution and the filtrate was controlled to 4. After the filtering procedure, the separation efficiency of the glucose and the zinc chloride (ZnCl$_2$) was 2.96, as shown in Table 4.

TABLE 4

| Examples | Operating pressure (kg/cm$^2$) | Separation efficiency |
|---|---|---|
| 17 | 26 | 1.77 |
| 18 | 30 | 2.40 |
| 19 | 35 | 2.55 |
| 20 | 40 | 2.96 |

In summary, selection of appropriate intercept molecular weight and operating pressure range of the nanofiltration membrane is capable of effectively reducing the effect of the convective mechanism while sugar or sugar derivatives pass through the membrane and reducing the mass transfer rate (enhancing the blocking effect).

Comparison of Separation Efficiency of Disaccharide Systems and Monosaccharide Systems

EXAMPLE 21

The Disaccharide System

A filtering procedure (total feed: 30 kg; operating pressure: 35 kg/cm$^2$; pH: 2) was performed on the hydrolysis sugar solution (glucose concentration: 3 wt %; xylose concentration: 1.5 wt %; zinc chloride concentration: 12 wt %) with a nanofiltration membrane (DOW FILMTEC™; model: NF-40). The ratio of the concentrated solution and the filtrate was controlled to 4. After the filtering procedure, the results were shown in Table 5.

EXAMPLE 22

The Monosaccharide System

A filtering procedure (total feed: 30 kg; operating pressure: 35 kg/cm$^2$; pH: 2) was performed on the hydrolysis sugar solution (glucose concentration: 3 wt %; zinc chloride concentration: 12 wt %) with a nanofiltration membrane (DOW FILMTEC™; model: NF-40). The ratio of the concentrated solution and the filtrate was controlled to 4. After the filtering procedure, the results were shown in Table 5.

TABLE 5

| | Disaccharide system | | Monosaccharide system |
|---|---|---|---|
| | Glucose | Xylose | Glucose |
| Initial concentration (wt %) | 3 | 1.5 | 3 |
| Separation efficiency | 23 | 13 | 7.9 |

Comparison of Separation Efficiency Under Various Sugar Concentrations

Example 23

A filtering procedure (total feed: 30 kg; operating pressure: 35 kg/cm$^2$; pH: 4.6) was performed on the hydrolysis sugar solution (glucose concentration: 3 wt %; zinc chloride concentration: 12 wt %) with a nanofiltration membrane (DOW FILMTEC™; model: NF-40). The ratio of the concentrated solution and the filtrate was controlled to 4. After the filtering procedure, the separation efficiency of the glucose and the zinc chloride (ZnCl$_2$) was 2.5, as shown in Table 6.

EXAMPLE 24

A filtering procedure (total feed: 30 kg; operating pressure: 35 kg/cm$^2$; pH: 4.6) was performed on the hydrolysis sugar solution (glucose concentration: 5.76 wt %; zinc chloride concentration: 12 wt %) with a nanofiltration membrane (DOW FILMTEC™; model: NF-40). The ratio of the concentrated solution and the filtrate was controlled to 4. After the filtering procedure, the separation efficiency of the glucose and the zinc chloride (ZnCl$_2$) was 5.0, as shown in Table 6.

TABLE 6

| Examples | Initial concentration of glucose (wt %) | Separation efficiency |
|---|---|---|
| 23 | 3 | 2.5 |
| 24 | 5.76 | 5.0 |

Tables 5 and 6 show that, while the total sugar concentration is high, even in various pH conditions, sugar and metal salts are still separated.

EXAMPLE 25

The Fermentation Test of the Hydrolysis Sugar Solution of the Hydrolysis Product of Biomass Sodium carbonate was added to a hydrolysis sugar solution containing zinc ions to generate zinc carbonate precipitate therein. After filtration, a sugar solution (total sugar concentration: 1.2 wt %; sodium chloride concentration: 0.6 wt %) was obtained. After 6 kg of the sugar solution and 19 kg of water were mixed and uniformly stirred, a filtering procedure (total feed: 25 kg; operating pressure: 35 kg/cm$^2$; pH: 7-8) was performed on the mixing solution with a nanofiltration membrane (DOW FILMTEC™; model: NF-40) to obtain 6 kg of a concentrated solution. Next, 19 kg of pure water was added to the concentrated solution. Another filtering procedure (including adding water and filtrating by membrane) using a nanofiltration membrane was repeated three times to obtain 3 kg of a concentrated solution. An alcohol fermentation test was carried out using the strains, Candida shehatae #21774, and the yield thereof was 40.91%, similar to the yield (38.5%) of the fermentation performed by the same strains of a simulated sugar solution. Table 7 shows that the hydrolysis sugar solution obtained by the separation method of the hydrolysis product of biomass of the present disclosure can be applied for fermentation.

TABLE 7

| | Sugar solution concentration 70 g/L (glucose:xylose = 2:1) | Simulated sugar solution (simulated hydrolysis sugar solution) | Bagasse hydrolysis sugar solution (Example 25) | Bagasse hydrolysis sugar solution (Example 25) |
|---|---|---|---|---|
| Yeast strains | | C. shehatae #21774 | | Y600 |
| Fermentation time (hr) | | 48 | 48 | 22 |
| Alcohol concentration (g/L) | | 16.8 | 18.9 | 14.9 |
| Alcohol yield (%)* | | 67.3 | 67.7 | 82 |

*NREL alcohol yield was 78%

In accordance with the present method for separating hydrolysis product, by adjusting the pH value of the hydrolysis sugar solution, the electrostatic interaction between zinc chloride and the membrane is reduced and the mass transfer of the divalent metal salts in the membrane is increased. In addition, selection of appropriate intercept molecular weight of the nanofiltration membrane is capable of reducing the effect of the convective mechanism while sugar or sugar derivatives through the membrane and reducing the mass transfer rate (enhancing the blocking effect). Furthermore, the operating pressure conditions are adjusted to enhance the driving force of water and water flux to facilitate the hydrolysis sugar solution requiring a sugar substance at a higher concentration (i.e. purity improvement) in the concentrated solution, and requiring a metal salt solution with higher purity in the filtrate, achieving an optimal separation effect between the metal salts and sugar or sugar derivatives.

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. A method for separating hydrolysis product of biomass, comprising:
   providing a mixture solution containing a hydrolysis product of biomass and a divalent metal salt, wherein the divalent metal salt comprises zinc chloride, calcium chloride, magnesium chloride or a combination thereof;
   adjusting a pH value of the mixture solution to between 1-4.6;
   performing a filtering procedure on the mixture solution using a nanofiltration membrane to obtain a retentate of a concentrated solution and a permeate of a filtrate,
   wherein the concentrated solution includes the hydrolysis product of biomass and the filtrate includes the divalent metal salt, and the concentration of the hydrolysis product of biomass in the retentate is greater than that of the hydrolysis product of biomass in the permeate,
   wherein the filtering procedure has an operating pressure of 26-40 kg/cm$^2$;
   wherein the nanofiltration membrane has 100-1,000 amu (Daltons) molecular weight cut-off; and
   wherein the nanofiltration membrane comprises polyamide.

2. The method for separating hydrolysis product of biomass as claimed in claim 1, wherein the hydrolysis product of biomass has a weight ratio of 0.01-30 wt % in the mixture solution.

3. The method for separating hydrolysis product of biomass as claimed in claim 1, wherein the divalent metal salt has a weight ratio of 1-20 wt % in the mixture solution.

4. The method for separating hydrolysis product of biomass as claimed in claim 1, wherein the hydrolysis product of biomass has a molecular weight of 100-400 daltons.

5. The method for separating hydrolysis product of biomass as claimed in claim 1, wherein the hydrolysis product of biomass comprises glucose, xylose, arabinose, cellobiose, 5-hydroxymethylfurfural (HMF), furfural (FF) or a combination thereof.

6. The method for separating hydrolysis product of biomass as claimed in claim 1, wherein the nanofiltration membrane has 200-400 amu (Daltons) molecular weight cut-off.

7. The method for separating hydrolysis product of biomass as claimed in claim 1, further comprising performing at least one filtering procedure on the concentrated solution.

8. The method for separating hydrolysis product of biomass as claimed in claim 7, wherein the hydrolysis product of biomass has a weight ratio of 1-10 wt % in the concentrated solution.

9. The method for separating hydrolysis product of biomass as claimed in claim 1, further comprising performing at least one filtering procedure on the filtrate.

10. The method for separating hydrolysis product of biomass as claimed in claim 9, wherein the divalent metal salt has a weight ratio of 0.1-20 wt % in the filtrate.

* * * * *